_United States Patent_ [19]

Franklin

[11] Patent Number: 4,824,601

[45] Date of Patent: Apr. 25, 1989

[54] LIQUID ANTIOXIDANT PRODUCED BY ALKYLATING DIPHENYLAMINE WITH A MOLAR EXCESS OF DIISOBUTYLENE

[75] Inventor: Janet Franklin, Rochdale, England

[73] Assignee: Ciba-Geigy-Corporation, Ardsley, N.Y.

[21] Appl. No.: 144,596

[22] Filed: Jan. 11, 1988

Related U.S. Application Data

[63] Continuation of Ser. No. 62,372, Jun. 12, 1987, which is a continuation of Ser. No. 779,891, Sep. 25, 1985, which is a continuation-in-part of Ser. No. 676,903, Nov. 30, 1984.

[30] Foreign Application Priority Data

Dec. 8, 1983 [GB] United Kingdom ............... 8332797

[51] Int. Cl.$^4$ .............................................. C09K 15/18
[52] U.S. Cl. ...................................... 252/401; 252/50; 564/409
[58] Field of Search ................... 252/401, 50; 564/409

[56] References Cited

U.S. PATENT DOCUMENTS

| | | | |
|---|---|---|---|
| 2,943,112 | 6/1960 | Popoff et al. | 564/409 |
| 3,201,486 | 8/1965 | Bielawski et al. | 564/409 |
| 3,496,230 | 2/1970 | Kaplan . | |
| 3,714,258 | 1/1973 | Bayha et al. | 564/409 |
| 4,163,757 | 8/1979 | D'Sidocky | 564/409 |
| 4,226,732 | 10/1980 | Reinhard et al. . | |
| 4,248,721 | 3/1981 | Jaffe . | |
| 4,351,958 | 9/1982 | Takahata et al. | 564/409 |

FOREIGN PATENT DOCUMENTS

| | | |
|---|---|---|
| 55-53249 | of 1980 | Japan . |
| 846226 | 8/1960 | United Kingdom . |
| 1143250 | 2/1969 | United Kingdom . |
| 1332201 | 10/1973 | United Kingdom ............... 252/401 |

OTHER PUBLICATIONS

ASTM D 2272-85.
Derwent Abstract No. 85-179087/30, (Jul. 24, 1985), "Prep. of Liq. Autioxidant from Diphenylamine and Excess Diisobutylene under Specific Reaction Conditions".

_Primary Examiner_—Matthew A. Thexton
_Attorney, Agent, or Firm_—Luther A. R. Hall

[57] ABSTRACT

Process is described for the production of a liquid antioxidant composition by reaction of diphenylamine with diisobutylene comprising reacting diphenylamine with diisobutylene in a molar ratio of from 1:1.1 to 1:2.5 and in the presence of an acid activated earth catalyst, while ensuring that the concentration of diisobutylene remains substantially constant throughout the reaction period at a reaction temperature of at least 160° C., the reaction being effected for such a period that the content of 4,4'-dioctyldiphenylamine in the reaction mass, excluding catalyst, is below 25% by weight; and removing catalyst and unreacted diisobutylene; the product of this process; and the use of this product as a stabilizer for organic material against oxidative degradation.

14 Claims, No Drawings

LIQUID ANTIOXIDANT PRODUCED BY ALKYLATING DIPHENYLAMINE WITH A MOLAR EXCESS OF DIISOBUTYLENE

CROSS REFERENCE

This is a continuation of application Ser. No. 062,372, filed on June 12, 1987, now abandoned, which is in turn a continuation of application Ser. No. 779,891, filed on Sept. 25, 1985, now abandoned, which is in turn a continuation-in-part of application Ser. No. 676,903, filed on Nov. 30, 1984, now abandoned.

DETAILED DESCRIPTION

The present invention relates to a process for the production of a liquid antioxidant composition; the product so produced and its use as a stabiliser in organic material.

It is known to produce a dark-coloured solid antioxidant composition by reacting diphenylamine with diisobutylene in the presence of aluminium chloride, as catalyst. The product so obtained contains approximately 90% by weight of di-t-octyl-diphenylamine and a total of about 10% by weight of mono-t-octyl- and mixed t-butyl-t-octyl diphenylamines.

Such solid antioxidant compositions are disadvantageous in terms of ease of handling and transportation, and readiness of incorporation into the substrate to be stabilised.

Liquid antioxidant compositions which are easily handled and incorporated, and derived from diphenylamine and olefines are also known e.g. from GB patent specification No. 1,332,201.

We have now found that, by reacting diphenylamine and diisobutylene under specific reaction conditions, we can produce a liquid antioxidant composition having outstanding antioxidant properties.

Accordingly, the present invention provides a process for the production of a liquid antioxidant composition, which process comprises reacting diphenylamine with a molar excess of diisobutylene in the presence of an activated earth catalyst, while ensuring that the concentration of diisobutylene remains substantially constant throughout the reaction period, at a reaction temperature of at least 160° C., the reaction being effected for such a period that the content of 4,4'-di-t-octyl-diphenydiphenylamine in the reaction mass, excluding catalyst, is below 25%; and removing catalyst and unreacted diisobutylene. When used in the present specification and claims, the term "t-octyl" is derived from 2,2,4-trimethyl-1-pentene and denotes 1,1,3,3-tetramethylbutyl. The reaction may be conveniently effected by charging the diphenylamine and catalyst into the reaction vessel and heating the mixture to a temperature of at least 160° C., preferably at least 165° C., preferably with stirring. Then the diisobutylene may be added to the hot mixture of diphenylamine and catalyst at such a rate that the temperature of the mixture does not fall below 160° C., preferably not below 165° C. Heating and stirring may be continued at a temperature of at least 160° C., with frequent sampling, until the product, excluding catalyst, contains less than 25% by weight of 4,4'-dioctyldiphenylamine.

Experiments have shown that if the reaction is stopped at points at which the amount of 4,4-dioctyldiphenylamine in the reaction mixture is above 25% by weight, then crystals form in the product on standing. The diphenylamine content of the reaction mixture quickly falls to below 10% by weight, moreover below 5% by weight and remains at this low level during the course of the reaction. Any conventional technique may be employed for effecting contact between a hot liquid reaction mixture and a liquid reactant boiling below the temperature of the hot liquid reaction mixture. Although conventional methods such as gravity feed of the diisobutylene below or close to the surface of the reaction mixture is a satisfactory technique, it is preferred to use a temperature-regulated metering pump in order to introduce the diisobutylene reactant. The temperature at which the process of the invention is effected is at least 160° C. and may be considerably higher e.g. up to 250° C. To reduce degradation risks, the maximum temperature used is usually about 190° C.

The time over which the diisobutylene reactant may be added to the hot mixture of diphenylamine and catalyst can vary over a wide range depending on the reaction temperature but is usually within the limits of 3 to 30 hours.

The molar ratio of diphenylamine to diisobutylene can also vary widely but is kept within the range of from 1:1.11 to 1:2.5 preferably from 1:1.3 to 1:1.75 in order to reduce raw material costs, and to minimise the addition times of diisobutylene.

The catalyst may be removed from the reaction mixture using any known method for separating a solid from a liquid, in particular any known filtration or centrifugation method. Catalyst recovery is conveniently carried out by vacuum filtration of the hot reaction mass. Likewise excess diisobutylene may be removed from the reaction mixture by any convenient method for separating liquids of different boiling points, in particular by fractional distillation. Recovery of excess diisobutylene reactant is readily accomplished by vacuum distillation of the reaction mixture.

The activated earth catalyst used in the process of the present invention preferably has a free moisture content below 10%, more preferably below 5% by weight.

Commercially-available catalysts which have proved effective include Fulcat®14, Fulmont®700C, Fulmont®237, Katalysator K10 (Sud-Chemie) and, especially Fulcat®22B (a sulphuric acid-activated Fullers Earth). The Fulcat and Fulmont catalysts are commercially-available from Laporte Industries.

Activated earth catalysts used according to the present process are advantageous over the known aluminium chloride catalysts in that:

(a) catalyst removal can be effected by simple filtration; and (b) activated earths, having-bleaching properties, provide end products which are much lighter in colour than those obtained using aluminium chloride catalysts.

The amount of catalyst used in the process of the present invention may vary widely without detriment to the course of the reaction. For practical purposes, however, we prefer to use catalyst amounts within the range of from 5% to 25%, more preferably from 5% to 15% by weight, based on the weight of diphenylamine reactant.

The products of the process of the present invention are believed to contain at least the following components:

(i) t-butylated diphenylamines;
(ii) t-octylated diphenylamines; and
(iii) higher alkylated diphenylamines.

The liquid antioxidants produced by the process of the present invention are useful as antioxidants in a wide range of organic materials.

Accordingly, the present invention further provides a composition comprising an organic material susceptible to oxidative degradation and, as stabiliser, a stabilising amount of a liquid product produced according to the process of the invention.

A particular class of organic materials susceptible to oxidative deterioration for which the products of the process of the invention are valuable as antioxidants, is that consisting of lubricants and functional fluids of mineral oil origin or synthetic lubricants or functional fluids, especially those derived from carboxylic esters and intended for use at temperatures at, or above 200° C.

Examples of synthetic lubricants include lubricants based on a diester of a dibasic acid and a monohydric alcohol, for instance dioctyl sebacate or dinonyl adipate; on a triester of trimethylol propane and a monobasic acid or mixture of such acids, for instance trimethylol propane tripelargonate, trimethylol propane tricaprylate or mixtures thereof; on a tetraester of pentaerythritol and a monobasic acid or mixture of such acids, for instance pentaerythritol tetracaprylate; or on complex esters derived from monobasic acids, dibasic acids and polyhydric alcohols, for instance a complex ester derived from trimethylol propane, caprylic acid and sebacic acid; or of mixture thereof.

Other synthetic lubricants are those known to the art-skilled and described e.g. in "Schmiermittel-Taschenbuch" (Huethig Verlag, Heidelberg 1974). Especially suitable, apart from the preferred mineral oils are e.g. phosphates, glycols, polyglycols, polyalkylene glycols and poly-alpha olefines.

Other organic materials susceptible to oxidative degradation for which the products of the process of the present invention are particularly valuable antioxidants, include, for instance, substances falling within the following groups:

(a) natural and synthetic polymeric materials, for instance natural rubber; synthetic addition polymers such as homopolymers and co-polymers of vinyl and vinylidene monomers, including ethylene, propylene, styrene, butadiene, isoprene, acrylonitrile, vinyl chloride or vinyl acetate; synthetic polymers derived from condensation reactions and containing ether, ester (ex carboxylic, sulphuric or carbonic acids) amide or urethane groupings, for instance alkyd and polyamide resins; in the case of these polymers, the liquid antioxidant may be incorporated during a polymer processing step, for instance during the compounding of rubber;

(b) non-polymeric oxygen-containing substances, for instance aldehydes such as n-heptaldehyde; and unsaturated fatty acids or esters thereof for instance methyl oleate and ricinoleic acid;

With regard to these other organic materials mentioned above, the antioxidants produced by the process of the invention are effective in the stabilisation of rubbers. They may be used in natural or synthetic rubbers. An example of a synthetic rubber is SBR (styrenebutadiene rubber).

Alternatively, the products may be used to stabilise a mixture of natural and synthetic rubber, for instance a blend of natural and styrene-butadiene rubber.

The antioxidant products of the process of the present invention may be employed in multi-ingredient compositions, that is compositions containing at least one organic substance susceptible to oxidative deterioration or a mixture thereof and one or more organic or inorganic compounds, for instance an alcoholic or aqueous emulsion of an organic material susceptible to oxidative deterioration.

The compositions of the present invention preferably contain a proportion of the liquid antioxidant produced according to the present invention within the range of from 0.05% to 5.0% by weight based on the weight of the organic material. More preferably, the compositions contain a proportion of the liquid antioxidant within the range of from 0.1% to 4.0% by weight based on the weight of the organic material. The amount of antioxidant product employed in any particular organic material will depend not only on the nature of the organic material but also on the external conditions under which the material is to be used. Thus organic materials to be used at normal temperatures will usually require a smaller proportion of the liquid antioxidant product than organic materials, such as synthetic lubricants designed for use at elevated temperatures.

In addition to the liquid antioxidant, a lubricant may also contain, in order to iprove certain applicational properties, other additive such as further antioxidants, metal passivators, rust inhibitors, viscosity index improvers, pour-point depressors, dispersants/surfactants or anti-wear additives.

EXAMPLES OF PHENOLIC ANTIOXIDANTS

1. Alkylated Monophenols 2,6-Di-tert.-butylphenol
2-tert.-butyl-4,6-dimethylphenol
2,6-Di-tert.-butyl-4-ethylphenol
2,6-Di-tert.-butyl-4-n-butylphenol
2,6-Di-tert.-butyl-4-i-butylphenol
2,6-Di-cyclopentyl-4-methylphenol
2-($\alpha$-Methylcyclohexyl)-4,6-dimethylphenol
2,6-Di-octadecyl-4-methylphenol
2,4,6Tri-cyclohexylphenol
2,6-Di-tert.-butyl-4-methoxymethylphenol

2. Alkylated Hydroquinone 2,6-Di-tert.-butyl-4-methoxyphenol
2,5-Di-tert.-butyl-hydroquinone
2,5-Di-tert.-amyl-hydroquinone
2,6-Diphenyl-4-octadecyloxyphenol

3. Hydroxylated Thiodiphenylethers 2,2'-Thio-bis-(6-tert.-butyl-4-methylphenol)
2,2'-Thio-bis-(4-octylphenol)
4,4'-Thio-bis-(6-tert.-butyl-3-methylphenol)
4,4'-Thio-bis-(6-tert.-butyl-2-methylphenol)

4. Alkylidene-Bisphenols 2,2'-Methylene-bis-(6-tert.-butyl-4-methylphenol)
2,2'-Methylene-bis-(6-tert.-butyl-4-ethylphenol)
2,2'-Methylene-bis-[4-methyl-6-($\alpha$-methylcyclohexyl)-phenol]
2,2'-Methylene-bis-(4-methyl-6-cyclohexylphenol)
2,2'-Methylene-bis-(6-nonyl-4-methylphenol)
2,2'-Methylene-bis-(4,6-di-tert.-butylphenol)
2,2'-Ethylidene-bis-(4,6-di-tert.-butylphenol)
2,2'-Ethylidene-bis-(6-tert.-butyl-4-isobutylphenol)
2,2'-Methylene-bis-[6-($\alpha$-methylbenzyl)-4-nonylphenol]
4,4'-Methylene-bis-(6-tert.-butyl-2-methylphenol)
1,1-Bis-(5-tert.-butyl-4-hydroxy-2-methylphenol)-butane 2,6-Di-(3-tert-butyl-5-methyl-2-hydroxybenzyl)-4-methylphenol 1,1,3-Tris-5-tert.-butyl-4-hydroxy-2-methylphenyl)-3-n-dodecyl-mercaptobutane Ethyleneglycol-bis[3,3-bis-(3'-tert.-butyl-4'-hydroxyphenyl)-butyrate]

Di-(3-tert.-butyl-4-hydroxy-5-methylphenyl)-dicyclopentadiene

Di-[3'-tert.-butyl-2'-hydroxy-5'-methyl-benzyl)-6-tert.-butyl-4-methyl-phenyl]-terephthalate

5. Benzyl Compounds 1,3,5-Tri-(3,5-di-tert.-butyl-4-hydroxybenzyl)-2,4,6-trimethylbenzene Di-(3,5-di-tert.-butyl-4-hydroxybenzyl)-sulfide Bis-(4-tert.-butyl-3-hydroxy-2,6-dimethylbenzyl)dithiol-terephthalate 1,3,5-Tris-(3,5-di-tert.-butyl-4-hydroxybenzyl)-isocyanate 1,3,5-Tris-(4-tert.-butyl-3-hydroxy-2,6-dimethylbenzyl)-isocyanurate 3,5-Di-tert.-butyl-4-hydroxybenzyl-phosphonic acid-dioctadecylester 3,5-Di-tert.-butyl-4-hydroxybenzyl-phosphonic acid-monoethylester Calcium-salt

6. Acylaminophenols

4-Hydroxy-lauric acid anilide
4-Hydroxy-stearic acid anilide
2,4-Bis-octylmercapto-6-(3,5-di-tert.-butyl-4-hydroxyanilino)-s-triazine
N-(3,5-di-tert.-butyl-4-hydroxyphenyl)-carbamic acid octyl ester

| 7. Esters of β-3,5-Di-tert.-butyl-4-hydroxyphenyl)-propionic acid with mono- or polyhydric alcohols e.g. with | |
|---|---|
| Methanol | Diethyleneglycol |
| Octadecanol | Triethyleneglycol |
| 1,6-Hexanediol | Pentaerythritol |
| Neopentylglycol | Tris-hydroxyethyl-isocyanurate |
| Thiodiethyleneglycol | Di-hydroxyethyl-oxalic acid diamide |
| 8. Esters of β-(5-tert.-butyl-4-hydroxy-3-methylphenyl)-propionic acid with mono- or polyhydric alcohols e.g. with | |
| Methanol | Diethyleneglycol |
| Octadecanol | Triethyleneglycol |
| 1,6-Hexanediol | Pentaerythritol |
| Neopentylglycol | Tris-hydroxyethyl-isocyanurate |
| Thiodiethyleneglycol | Di-hydroxyethyl-oxalic acid diamide |

9. Amides of
β-3,5-Di-tert.-butyl-4-hydroxyphenyl)-propionic acid e.g.

N,N'-Di-(3,5-di-tert.-butyl-4-hydroxyphenylpropionyl)-hexamethylene-diamine

N,N'-Di-(3,5-di-tert.-butyl-4-hydroxyphenylpropionyl)-trimethylene-diamine

N,N'-Di-(3,5-di-tert.-butyl-4-hydroxyphenylpropionyl)-hydrazine

Examples of amine antioxidants

N,N'-Di-isopropyl-p-phenylenediamine
N,N'-Di-sec.-butyl-p-phenylenediamine
N,N'-Bis(1,4-dimethyl-pentyl)-p-phenylenediamine
N,N'-Bis(1-ethyl-3-methyl-pentyl)-p-phenylenediamine
N,N'-Bis(1-methyl-heptyl)-p-phenylenediamine
N,N'-Dicyclohexyl-p-phenylenediamine
N,N'-Diphenyl-p-phenylenediamine
N,N'-Di-(naphthyl-2-)-p-phenylenediamine
N-Isopropyl-N'-phenyl-p-phenylenediamine
N-(1,3-Dimethyl-butyl)-N'-phenyl-p-phenylenediamine
N-(1-Methyl-heptyl)-N'-phenyl-p-phenylenediamine
N-Cyclohexyl-N'-phenyl-p-phenylenediamine
4-(p-Toluene-sulfonamido)-diphenylamine
N,N'Dimethyl-N,N'-di-sec.-butyl-p-phenylenediamine
Diphenylamine
4-Isopropoxy-diphenylamine
N-Phenyl-1-naphthylamine
N-Phenyl-2-naphthylamine
octylated Diphenylamine
4-n-Butylaminophenol
4-Butyrylamino-phenol
4-Nonanoylamino-phenol
4-Iodecanoylamino-phenol
4-Octadecanoylamino-phenol
Di-(4-methoxy-phenyl)-amine
2,6-Di-tert.-butyl-4-dimethylamino-methyl-phenol
2,4'-Diamino-diphenylmethane
4,4'-Diamino-diphenylmethane
N,N,N',N'-Tetramethyl-4,4'-diamino-diphenylmethane
1,2-Di-(phenylamino)-ethane
1,2-Di-[(2-methyl-phenyl)-amino]-ethane
1,3-Di-(phenylamino)-propane
(o-tolyl)-biguanide
Di-[4-(1',3'-dimethyl-butyl)-phenyl]amine Examples of metal passivators are for copper e.g.

Benztriazole and derivatives thereof, Tetrahydrobenztriazole,

2-Mercaptobenzthiazole, 2,5-Dimercaptothiadiazole, Salicylidenepropylenediamine, Salts of Salicylaminoguanidine.

Examples of rust inhibitors are:

(a) Organic acids, their esters, metal salts and anhydrides e.g. N-Oleoyl-sarcosine, Sorbitan-mono-oleate, lead-naphthenate, Dodecenyl-succinic anhydride, 4-Nonyl-phenoxy-acetic acid.

(b) nitrogen-containing compounds e.g.

I. Primary, secondary or tertiary aliphatic or cycloaliphatic amines and amine-salts of organic and inorganic acids e.g. oil-soluble alkylammonium carboxylates II. Heterocyclic compounds e.g. Substituted Imidazolines and Oxazolines (c) Phosphorus-containing compounds e.g.

Amine salts of phosphonic acid partial esters (d) Sulfur-containing compounds e.g.

Barium-dinonylnaphthalene-n-sulfonates, calcium petroleum sulfonates

Examples of viscosity-index improvers are e.g.

Polymethacrylates, Vinylpyrrolidone/Methacrylate-Copolymers,

Polybutenes, Olefin-Copolymers, Styrene/Acrylat-Copolymers

Examples of pour-point depressants are e.g.

Polymethacrylates, or alkylated Naphthalene derivatives.

Examples of dispersants/surfactants are e.g.

Polybutenylsuccinic acid-imides, Polybutenylphosphonic acid derivatives, basic Magnesium-, Calcium-, and Bariumsulfonates and -phenolates.

Examples of anti-wear additives are e.g.

Sulfur and/or Phosphorus and/or Halogen containing compounds e.g. sulfurised vegetable oils, zinc dialkyldithiophosphates, Tritolylphosphate, chlorinated Paraffins, Alkyl- and Aryldisulfides.

The following Examples illustrate the invention in more detail.

EXAMPLE 1

169.2 g Diphenylamine and 33.8 g of an activated earth (Fulcat® 22B from Laporte Industries) are charged into a reaction vessel equipped with stirring- and temperature detecting means, and the mixture is heated to 165° C. Once the mixture is sufficiently mobile, the stirrer is put into operation. 196.4 g diisobutylene is then added gradually, at such a rate that the temperature of the reaction mixture does not drop below 165° C. The addition requires 5 hours for completion. Reflux commences soon after the start of the addition. Heating and stirring is continued at 165° C. with frequent sampling until gas/liquid chromatographic analysis shows that the content of 4,4'-dioctyldiphenylamine is below 25% (excluding catalyst).

The reaction mass is cooled to 60° C. and the catalyst is removed by vacuum filtration. The filtrate is transferred to a distillation apparatus and heating and stirring are commenced and the pressure is reduced to 26 mbar. Throughout the distillation, the internal temperature is slowly allowed to rise to 165° C. and is held at this temperature for two hours, during which distillation ceases. 300 g of a viscous, dark liquid are obtained having flash point 210° C.

EXAMPLES 2 TO 6

The reaction conditions employed in Example 1 are varied in terms of temperature range and ratio used of diphenylamine (DPA) to diisobutylene (DIB).

The results are set out in the following Table 1.

TABLE 1

| Example | Temperature range °C. | Molar ratio DPA to DIB | DIB addtn time (hours) | Total reaction time (hours) | Physical state of product |
|---|---|---|---|---|---|
| 2 | 160–170 | 1:2.5 | 5 | 29 | liquid |
| 3 | 169–170 | 1:2.5 | 19 | 24 | liquid |
| 4 | 168–170 | 1:2.1 | 30 | 30 | liquid |
| 5 | 165–170 | 1:2.0 | 17 | 30 | liquid |
| 6 | 160–170 | 1:2.0 | 6.25 | — | liquid |

What is claimed is:

1. Process for the production of a liquid antioxidant composition by reaction of diphenylamine with diisobutylene comprising reacting diphenylamine with diisobutylene in a molar ratio from 1:1.1 to 1:2.5 in the presence of an acid-activated earth catalyst, at a reaction temprature of at least 160° C., the reaction being effected for such a period that the content of 4,4'-di-t-octyldiphenylamine in the final reaction mass, excluding catalyst, is below 25% by weight and that of diphenylamine is below 10% by weight; and removing catalyst and unreacted diisobutylene thereby producing the desired liquid antioxidant composition.

2. Process according to claim 1 wherein the temperature at which the process is effected is within the range of from 160° C. to 250° C.

3. Process according to claim 2, wherein the temperature at which the process is effected is within the range of from 160° C. to 190° C.

4. Process according to claim 1 wherein the molar ratio of diphenylamine to diisobutylene is within the range of from 1:1.3 to 1:1.75.

5. Process according to claim 1 wherein the activated earth catalyst used has a free moisture content below 10% by weight.

6. Process according to claim 5 wherein the activated earth catalyst used has a free moisture content below 5% by weight.

7. Process according to claim 1 wherein the catalyst is a sulphuric acid-activated Fullers Earth.

8. Process according to claim 1 wherein the amount of catalyst used is from 5 to 25% by weight, based on the weight of diphenylamine reactant.

9. Process according to claim 8 wherein the amount of catalyst used is from 5 to 15% by weight, based on the weight of diphenylamine reactant.

10. Liquid antioxidant composition produced by reacting diphenyl-amine with diisobutylene in a molar ratio of 1:1.1 to 1:2.5 in the presence of an acid-activated earth catalyst, at a reaction temperature of at least 160° C., the reaction being effected for such a period that content of 4,4'-di-t-octyldiphenylamine in the final reaction mass, excluding catalyst, is below 25% by weight and that of diphenylamine is below 10% by weight; removing catalyst and unreacted diisobutylene; and isolating the resulting product.

11. Composition comprising an organic material susceptible to oxidative degradation and, as stabiliser, a stabilising amount of a liquid product according to claim 10.

12. Composition according to claim 11 wherein the organic material is a lubricant or functional fluid.

13. Composition according to claim 11 wherein the proportion of liquid antioxidant according to claim 11 is within the range of from 0.05% to 5% by weight, based on the weight of the organic material.

14. Composition according to claim 12 wherein the organic material is a lubricant and also comprises one or more of a further antioxidant, metal passivator, rust inhibitor, viscosity index iprover, pour-point depressor, dispersant/surfactant or anti-wear additive.

* * * * *